United States Patent [19]
Peterson et al.

[11] Patent Number: 5,197,477
[45] Date of Patent: Mar. 30, 1993

[54] ULTRASONIC DOPPLER FLOW MEASUREMENT SYSTEM WITH TISSUE MOTION DISCRIMINATION

[75] Inventors: Roy B. Peterson, Redmond; Jeffry E. Powers, Lake Stevens, both of Wash.

[73] Assignee: Advanced Technology Laboratories, Inc., Bothell, Wash.

[21] Appl. No.: 596,838

[22] Filed: Oct. 12, 1990

[51] Int. Cl.⁵ .............................................. A61B 8/00
[52] U.S. Cl. .......................... 128/661.08; 128/660.05; 128/660.06; 128/662.01
[58] Field of Search ...................... 128/661.08, 661.09, 128/662.01, 660.05, 660.06

[56] References Cited

U.S. PATENT DOCUMENTS

| | | | |
|---|---|---|---|
| 4,324,258 | 4/1982 | Huebscher | 128/661.09 |
| 4,485,821 | 12/1984 | Iinuma | 128/661.09 |
| 4,509,525 | 4/1985 | Seo | 128/661.09 |
| 4,651,742 | 3/1987 | Namekawa et al. | 128/662.01 |
| 4,683,893 | 8/1987 | Mayo | 128/660.06 |
| 4,790,323 | 12/1988 | Leavitt et al. | 128/661.09 |
| 4,850,364 | 7/1989 | Leavitt | 128/661.09 |
| 4,866,613 | 9/1989 | Amemiya et al. | 128/662.01 |
| 4,896,674 | 1/1990 | Seo | 128/661.09 |
| 4,928,698 | 5/1990 | Bonnefous | 128/661.08 |
| 4,961,427 | 10/1990 | Namekawa et al. | 128/661.09 |
| 4,972,838 | 11/1901 | Yamazaki | 128/660.05 |

Primary Examiner—Francis Jaworski
Assistant Examiner—George Manuel
Attorney, Agent, or Firm—W. Brinton Yorks, Jr.

[57] ABSTRACT

An ultrasonic diagnostic system for measuring fluid flow velocities through Doppler techniques is provided which eliminates the effects of tissue motion from fluid flow velocity information. In a preferred embodiment Doppler information signal are discriminated to determine the presence of signal components resulting from moving tissue, which signal components are located at frequencies of a Doppler spectrum other than the predetermined frequency location of stationary tissue signals. The tissue motion signal components present are shifted to the predetermined frequency location and removed by high pass filtering the Doppler signals. The remaining signals are then shifted back to their original frequency location and transmitted to a Doppler velocity estimator for further processing of the fluid flow velocity information and ultimate display of the information. To overcome problems of Doppler frequency inaccuracies at discrete spatial positions, the Doppler signals from a plurality of neighboring spatial locations are examined in the aggregate to determine the frequency location of tissue motion signal components.

20 Claims, 6 Drawing Sheets

ULTRASONIC DOPPLER FLOW MEASUREMENT SYSTEM WITH TISSUE MOTION DISCRIMINATION

This invention relates to ultrasonic diagnostic systems which measure the flow of fluids through Doppler interrogation and, in particular, to the discrimination of tissue motion by such systems.

Ultrasonic diagnostic systems which measure the flow of fluids through Doppler interrogation are in widespread use for the acquisition of medical patient data concerning the flow of blood and other fluids in the body. In one commonly accepted embodiment of Doppler measurement, an area of the body such as the heart is repetitively interrogated with ultrasonic waves and returning echo signals are compared to a reference to determine the velocity of blood flow in the heart. This interrogation is performed over a two-dimensional sector of the heart to determine flow velocities throughout the interrogated area. The resultant flow velocity values are then displayed in a color image format as a function of measurement location, where different shades and intensities of color represent blood flow of different velocities and directions. Such systems are commercially available as what are known as ultrasonic color flow imaging systems.

Such Doppler systems operate by measuring velocity in terms of relative motion between the fluids being interrogated and the scanhead which produces the ultrasonic waves and detects the resultant echo signals. However, Doppler information signals are returned not only by fluids, but also by tissue structure within the body. These latter signal components are undesired in systems where only fluid motion is being interrogated. But the prior art systems perform well when the scanhead is held stationary and the only substance moving in the interrogated area is the fluid which is being measured. This is because techniques are known for removing signal components returned from stationary tissue, and are generally embodied in what are referred to as clutter rejection filters. However, if the scanhead is moved even momentarily by the user, relative motion will occur between all of the tissue in the body and the scanhead, returning velocity-encoded echoes from throughout the interrogated area. Moreover, even if the scanhead is held stationary, tissue motion caused by the beating heart or breathing will return velocity-encoded echoes. These undesired velocity signals can be detected by the Doppler system even with the use of known clutter rejection filters, and the resulting artifacts will interfere with the fluid flow image, in which only the motion of the fluid being interrogated is desired. Hence it is desirable to eliminate these motion artifact components from the color flow image.

Previous attempts at eliminating these motion artifact effects have focused on their manifestation in the color images, which are displayed as a realtime sequence of fields or frames of Doppler flow velocity data. These efforts have employed image post-processing techniques to look for the occurrence of such artifacts from one image to another, and through frame to frame analytical techniques have attempted to eliminate the effects of the artifacts. Such techniques by their nature allow the ultrasound system to process the Doppler information through Doppler velocity determination and two-dimensional image formatting, thereby processing the undesired tissue motion artifacts along with the desired Doppler velocity information through most of the system data processing network. It would be desirable to eliminate such tissue motion artifact effects prior to image formatting, and most preferably prior to the determination of fluid Doppler velocity values in such systems.

In accordance with the principles of the present invention, an ultrasonic Doppler flow measurement system is provided which discriminates tissue motion artifacts prior to image formatting of detected velocity values and, in a preferred embodiment, prior to determination of Doppler velocity values. An embodiment of the present invention operates on Doppler data prior to image formatting by first discriminating those signal components resulting from tissue motion. The discriminated components are then eliminated from the Doppler spectrum and the resultant data is then processed for the determination of flow velocity information and image formatting. In a first embodiment the data being discriminated is the Doppler data relating to one location being interrogated for flow velocity, and in a preferred embodiment the data being discriminated relates to a plurality of positionally associated interrogation locations. A constructed embodiment of the present invention will obviate the need to perform Doppler velocity estimation and image processing of Doppler data which is contaminated with tissue motion artifacts.

In the drawings

Figure 1:
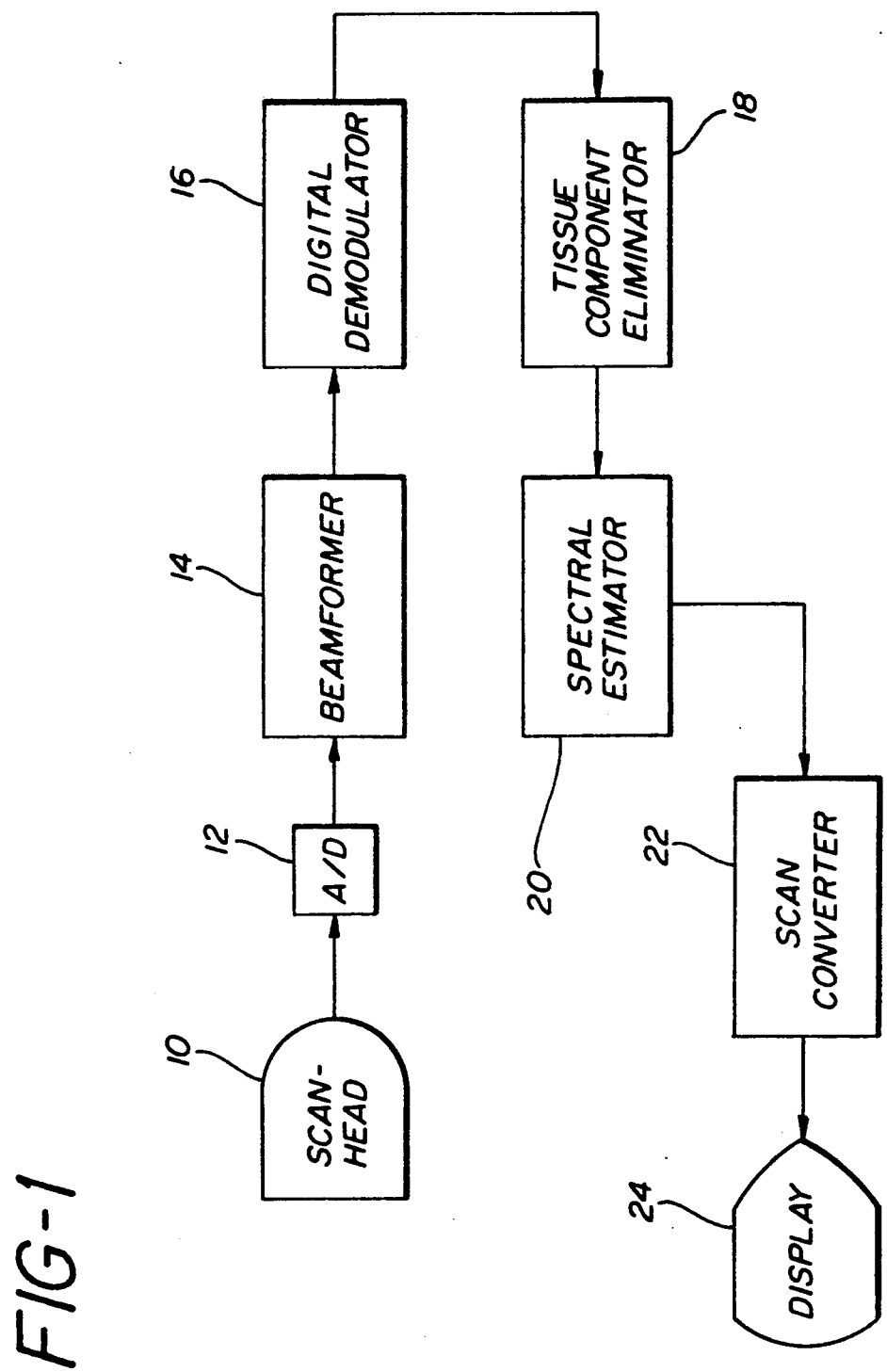
FIG. 1 illustrates in block diagram form an ultrasonic Doppler flow measurement system constructed in accordance with the principles of the present invention.

Referring first to FIG. 1, an ultrasonic diagnostic system for measuring the flow rates of fluids in the body of a patient and constructed in accordance with the principles of the present invention is shown in block diagram form. A scanhead 10 containing one or more piezoelectric transducer elements transmits ultrasonic waves into the body of a patient and receives ultrasonic echoes returned by the tissue and fluid structures of the body. The returning echoes are converted to electrical signals by the transducer(s) and the signals are then digitized by an analog to digital converter 12. A plurality of such digital signal samples are combined in a beamformer 14 to form coherent ultrasonic information signals which are coupled to a digital demodulator 16. The fluid flow velocity information contained in the ultrasonic information signals is encoded as phase shifts of the returning echo signals in relation to a reference signal. Accordingly the demodulation process involves a translation of the ultrasonic information signals to an intermediate frequency range and the resolution of the phase information into two components, an in-phase (I) component and a quadrature (Q) component. The output of the digital demodulator 16 thus is a stream of corresponding I and Q phase information signals containing information as to the velocity of fluids and tissue in the patient's body.

In accordance with the principles of the present invention, the phase information signals are applied to a tissue component eliminator 18. The tissue component eliminator processes the signals by discriminating signal components representing the motion of tissue relative to the scanhead 10, and eliminating these components from the Doppler spectrum. I and Q velocity information signals from which the effects of tissue motion have been removed are produced at the output of the tissue component eliminator.

The I and Q information signals from which the tissue signal components have been removed are applied to a spectral estimator 20, which determines the fluid velocities as represented by the Doppler content of the signals. The velocity information signals produced by the spectral estimator 20 are then applied to a scan converter where, in a preferred embodiment, the velocity information is translated to a color and an intensity and stored locationally as a function of the position in the scanned area of the body at which the measurement was taken. The scan converter thus arranges the flow velocities in an image format suitable for a color flow image, and the image is then displayed on an image display 24. Other image formats such as numerical and graphical representations may also be employed to display the flow velocities to the user.

Figures 2, 3:
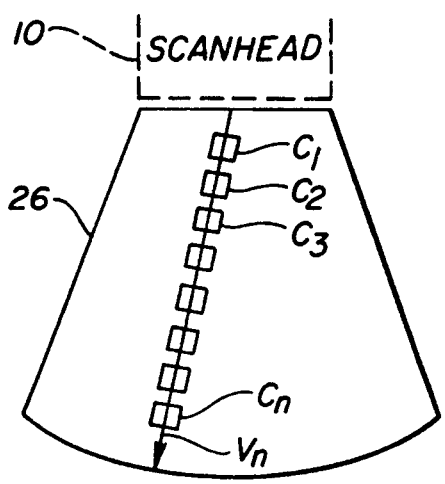
FIG. 2 illustrates an area being interrogated for Doppler flow information.
FIG. 3 illustrates an array of data values resulting from Doppler interrogation along an ultrasonic vector.

FIG. 2 depicts the manner in which Doppler data may be acquired to form a color flow image. The scanhead 10 sequentially transmits ultrasonic pulses in a plurality of vector directions over the scanned area 26 of the patient's body. One of these vector directions is indicated by arrow $V_n$ in FIG. 2. As echoes are returned from tissue and fluids along direction $V_n$, signal samples are taken from echoes returning from sequential positions along the vector. These positions are referred to herein as range cells, some of which are labelled $C_1$, $C_2$, $C_3$, ... $C_n$ in the Figure. The signal samples are processed by the beamformer 14 and converted by the digital demodulator 16 to I and Q quadrature signal samples.

This sequence of pulse transmission and echo reception is repeated a number of times along vector direction $V_n$. The transmitted pulses of four of these sequences are labelled $P_1$, $P_2$, $P_3$, and $P_4$ in the chart of FIG. 3. The I,Q echo samples taken in response to each of these pulse transmissions are shown below each pulse in FIG. 3. Each horizontal row of I,Q samples in FIG. 3 thus represents signal samples taken at a particular range cell location $C_1$ ... $C_n$, but at different points in time. An array of data of the form illustrated in FIG. 3 is operated upon by the tissue component eliminator 18 to remove the effects of tissue motion from the signals.

Figure 4A:
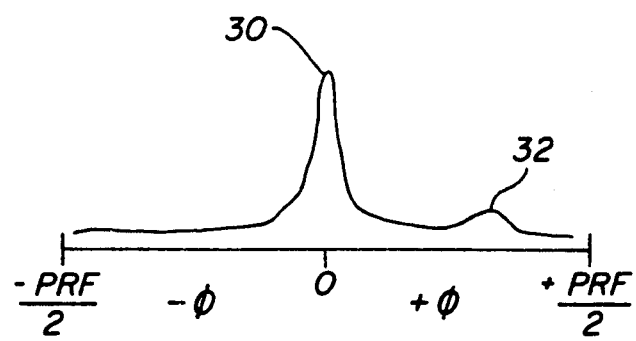
FIGS. 4a and 4b illustrate two Doppler spectra containing tissue motion signal components.

The Doppler velocity information content of the I,Q signal samples may be understood by reference to a representative Doppler spectrum as shown in FIG. 4a. This spectrum is shown as bounded by end points $-PRF/2$ and $+PRF/2$ although as will be subsequently explained the spectrum is a continuum through these end points. The end points $-PRF/2$ and $+PRF/2$ are the Nyquist limits of the signal sampling rate at a particular range cell, the sampling rate being the pulse repetition freguency (PRF) of pulses $P_1$, $P_2$, $P_3$, etc. of FIG. 3. In the center of the spectrum is DC, or zero, the Doppler frequency of tissue and fluids at rest. The Doppler phase information contained in the I,Q samples increases in the positive sense $(+\phi)$ or negative sense $(-\phi)$ toward the limit values from zero, depending on the velocity of the material at the range cell and its direction.

The waveform of FIG. 4a is seen to contain two peaks, a major one 30 and a lesser one 32. The major peak 30 results from echo information returned by tissue and the minor peak 32 results from echo information returned by a fluid such as blood. Peak 30 may be as much as 60-80 dB greater than peak 32 because tissue is a much stronger reflector of ultrasonic waves than blood. In FIG. 4a peak 30 is located at zero, a condition that exists when the reflecting tissue is substantially at rest, that is, there is substantially no motion component from the tissue. Elimination of the spectral components of peak 30 may be accomplished by high pass filtering the signals of the waveform of FIG. 4a, as the skirts of the rejection band defined by the high pass filter will be displaced symmetrically about zero, the frequency about which the signal components of peak 30 resulting from substantially stationary tissue are displaced. This known technique is in current use, as conventional color flow systems have a need to eliminate signals returned by stationary structures prior to operating on the Doppler flow content of the signals. Signal components resulting from substantially stationary tissue structure are not within the definition of "tissue motion components" as that term is used herein.

Figure 4B:
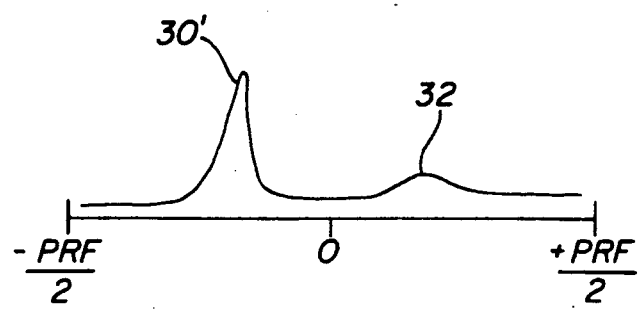

The problem confronted by the present invention is spectrally represented by FIG. 4b. In this Figure moving tissue has generated the signal components comprising peak 30'. FIG. 4b differs from FIG. 4a in that the peak 30' is displaced from zero by reason of the motion of the tissue. In this example, the blood velocity peak 32 is displaced on the opposite side of the zero reference by approximately the same magnitude as the displacement of peak 30'. An effort to remove the signal components comprising peak 30', as by notch or high pass filtering, would also eliminate the signal components comprising the blood velocity peak 32 by reason of the spectrally symmetrical effect of the filter. In sum, a process premised on the assumption that the tissue component is closer to zero than the blood flow component is ineffective in dealing with tissue motion in this situation.

Figure 5A:
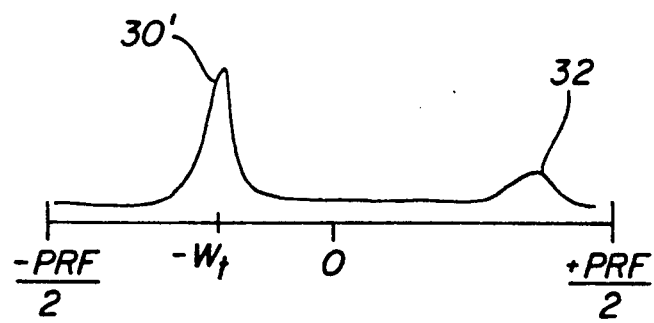
FIGS. 5a-5d illustrate a process for removing tissue motion signal components from a Doppler spectrum in accordance with the principles of the present invention.
Figure 5B:
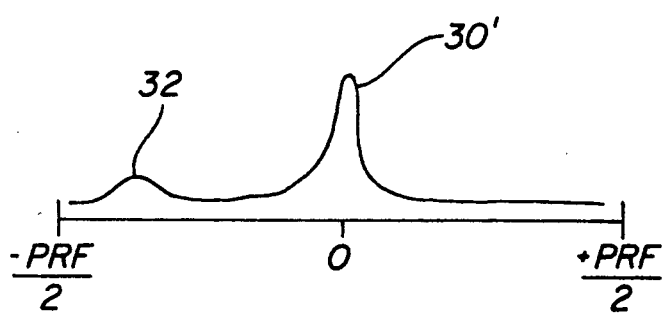

A technique for overcoming this problem in accordance with the principles of the present invention is illustrated by the spectra of FIGS. 5a-5d. In the first step of the inventive technique, the frequency location $\omega_t$ of the tissue motion component 30' in FIG. 5a is determined. Once the location of the tissue component is determined, the signals of the entire Doppler spectrum are modulated by the frequency deviation of the tissue component such that the tissue motion component becomes located at zero, as shown in FIG. 5b. Due to the continuity of the spectrum through the positive and negative Nyquist limits, this spectral shift of the signal components results in a "wrap around" of a portion of the spectral content. In the illustrated example, the blood flow component 32 of FIG. 5a is wrapped around $+PRF/2$ and through $-PRF/2$ so that the blood flow component appears at the left side of the spectrum in FIG. 5b after modulation.

Figure 5C:
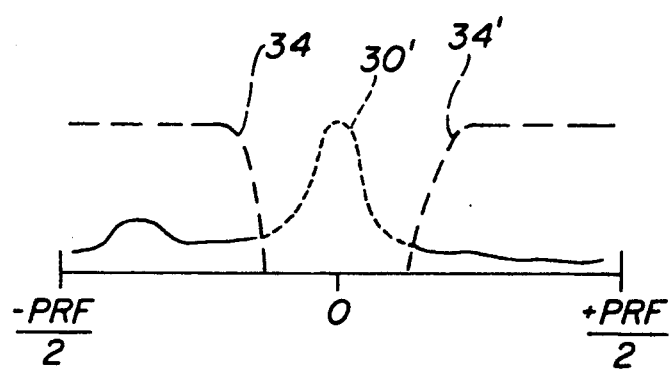

With the tissue motion component 30' now centered about zero, the spectral data is high pass filtered to remove the tissue component. The skirts 34, 34' of the high pass filter are shown in FIG. 5c, and the spectral content between the skirts as shown in dotted lines is effectively notched out of the spectrum.

With the tissue motion component thus eliminated, the spectral data is remodulated to relocate the blood flow component at its original spectral position. This is accomplished by remodulating the signals by the same deviation $\omega_t$ used above in FIG. 5b, but in an opposite sense.

Figure 5D:
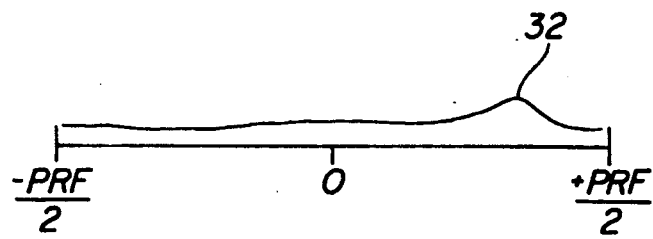

In this example, the original modulation was by the deviation $+\omega_t$, and thus the remodulation is by the value $-\omega_t$. The spectral result of this remodulation is shown in FIG. 5d. With the tissue component thus removed from the flow velocity data, the signal information can now be operated upon to determine the detected flow of blood without contamination by the effects of tissue motion.

Figure 6:
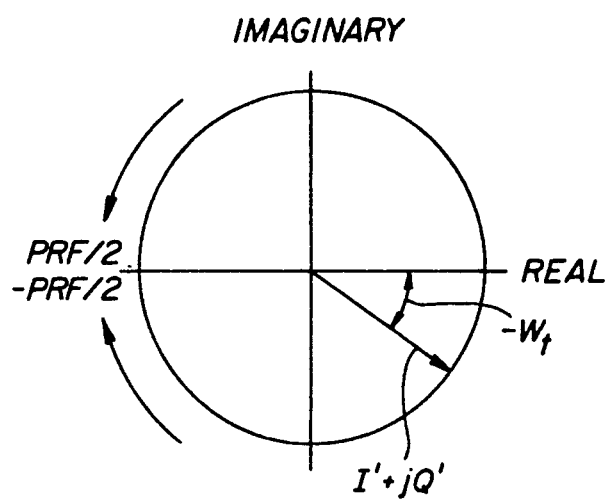
FIG. 6 is a phase diagram illustrating the discrimination of tissue motion signal components in accordance with the principles of the present invention.

Digital apparatus for performing the inventive technique for eliminating the effects of tissue motion may be constructed to operate upon digital I,Q signal data in the following manner. A number of known digital techniques may be used to discriminate the location of the tissue component, a preferred one being an autocorrelator. This autocorrelator operates by creating an offset alignment of the I,Q samples from the range cell location being investigated with the complex conjugate of itself. Taking the I,Q data of range cell $C_1$ of FIG. 3 for example, the offset alignment would appear as:

$I_{10}, Q_{10} \quad I_{11}, Q_{11} \quad I_{12}, Q_{12} \quad I_{13}, Q_{13}$ $I_{10}, -Q_{10} \quad I_{11}, -Q_{11} \quad I_{12}, -Q_{12} \quad I_{13}, -Q_{13}$ Vertically aligned samples are multiplied together and the products aggregated to form a result of the complex form $I' + jQ'$ Using this complex result the arc tangent is calculated using $Q'/I'$, and the result is the frequency of the tissue motion component expressed in radians, the angle $\omega_t$. Stated another way, the correlator has estimated the mean velocity of the tissue component, $\omega_t$, and this processing can be expressed mathematically as $$X = \sum_{k=1}^{n-1} X_{k-1} \cdot X_k^*,$$

assuming $X_k = I_k + jQ_k$, where n is the number of samples and * indicates complex conjugate. FIG. 6 shows a phase diagram on which the complex value $I' + jQ'$ is indicated, and the tissue component frequency $-\omega_t$ for the example of FIG. 5a. The left-hand end of the abcissa of the diagram is equal to both $+PRF/2$ and $-PRF/2$, the end limits of the linearly drawn spectra discussed previously. Through modulation of the $I' + jQ'$ complex value the arrow shown in the Figure could be swept continuously around the diagram in either a clockwise or counterclockwise direction, passing through the limits $+PRF/2$ and $-PRF/2$ as it does so. It is this mathematical principle which causes the wrap around of data from one end of the linearly drawn spectrum to the other as mentioned above in conjunction with FIG. 5b.

Figure 7:
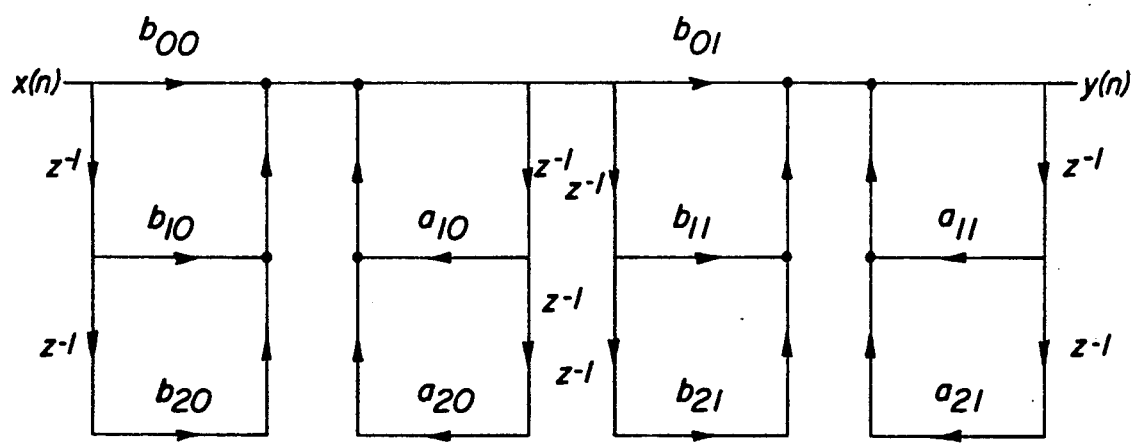
FIG. 7 illustrates a digital filter for eliminating tissue motion signal components in accordance with the principles of the present invention.

The spectral data is modulated to shift the tissue motion component to zero by multiplying the I,Q data of the range cell location by a sampled complex sinusoid. This is done by multiplying the I,Q data of the cell by the complex expression $\cos \theta + j \sin \theta$, where $\theta$ is equal to $+\omega_t$ determined by the correlator above. With the data thus shifted in frequency, it is filtered by processing by a high pass digital filter, a preferred one of which is the infinite impulse response (IIR) high pass filter diagrammatically shown in FIG. 7. In an actual implementation, the I and Q data samples are processed through initialized parallel filters of this form. The input data to the IIR filter, either I or Q, is applied at the input x(n), and the filtered data is produced at the output y(n). In FIG. 7 the a and b terms designate multiplying coefficients by which the data values are multiplied in determination of the filter response characteristics, $Z^{-1}$ indicates a single time interval shift delay, and the dotted nodes are points at which data arriving from two paths of the filter are summed. The exact characteristics of the high pass filter cutoff are application dependent, in consideration of the extent of the expected motion artifact.

Following removal of the tissue motion component content of the data by the high pass filter, the data is remodulated in the same way it was modulated, but using a frequency of the opposite sense as above in the complex expression. That is, $+\omega_t$ is replaced by $-\omega_t$, or the reverse, as appropriate. The spectral signal content is thereby shifted back to its original frequency domain location but with the effects of tissue motion removed.

It has been found that the accuracy of received Doppler information can vary from time to time as a result of random scattering effects and other factors. Such inaccuracies can result in the imprecise determination of the frequency location of the tissue motion component for a particular range cell. However, the present inventors have further found that, on the average, there is only a small deviation in the frequency location of the tissue component from one range cell to an adjacent range cell. The present inventors have taken advantage of this latter finding to overcome the aforementioned problem of tissue component locational inaccuracies. In accordance with a further aspect of the present invention, the discrimination of tissue component location is accomplished by first determining the complex value $I' + jQ'$ of the I,Q data from a number of neighboring range cells. For instance, $I' + jQ'$ can be determined for each of range cells $C_1-C_4$ in FIG. 3. The complex values are then accumulated in a summation of the form $I'_{(sum)} + jQ'_{(sum)}$ and this accumulated complex value is then used in the arc tangent calculation to determine $\omega_t$ for one or more of cells $C_1-C_4$. In this way the correlation of tissue component location between neighboring range cells is utilized to resolve inaccuracies in Doppler signals at particular range cell locations.

Figure 8:
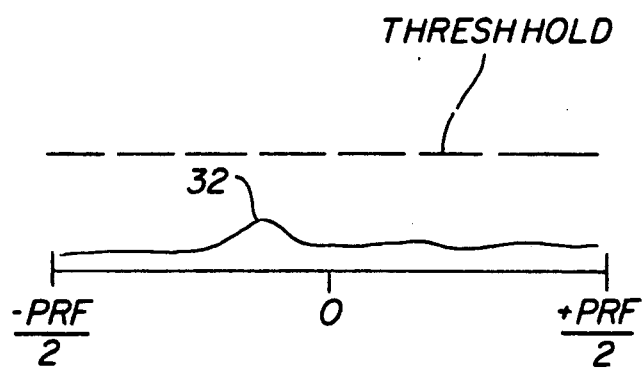
FIGS. 8 and 9 illustrate Doppler spectra in which the absence of tissue motion signal components is discriminated.

Another problem that may be encountered in an implementation of the present invention is the reception of signal components containing only desired flow information, devoid of any tissue component contamination. Such information reception may occur, for instance, when the range cell is at the center of a chamber of the heart, where only blood flow is present. This condition is spectrally represented in FIG. 8. In such a case it may be desirable to inhibit operation of a system of the present invention, and it would certainly be desirable not to eliminate the blood flow component as though it were a tissue component. In accordance with a further aspect of the present invention, the present inventors have made use of their recognition of the disparity in characteristics between tissue motion components and fluid flow components (e.g., signal strength, bandwidth) in applying a threshhold comparison before inplementation of the technique of the present invention. As illustrated in FIG. 8, when the components of the spectrum do not exceed the threshhold, the inventive system is inhibited so that the blood flow component 32 is not inadvertently removed from the spectrum.

Figure 9:
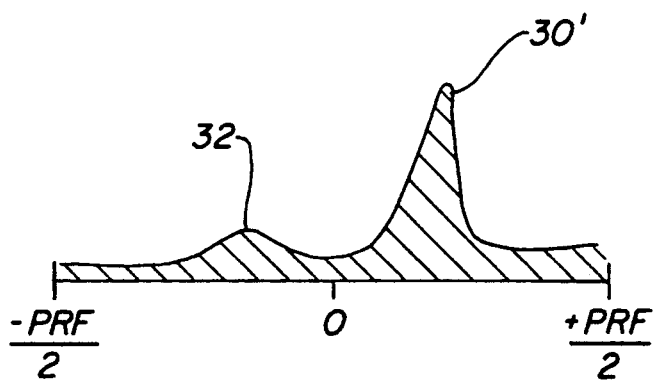

A preferred technique for implementing this threshhold comparison is to measure the power content of the Doppler spectrum. This may be accomplished digitally by integrating the received data values to effectively find the area under the curve containing the Doppler components. In FIG. 9, this area is shown by the diagonal lines under the spectral curve. The measured magnitude of the area is compared with a threshhold value and if the value is not exceeded, the tissue component eliminator is inhibited from removing any spectral signal content.

Figure 10:
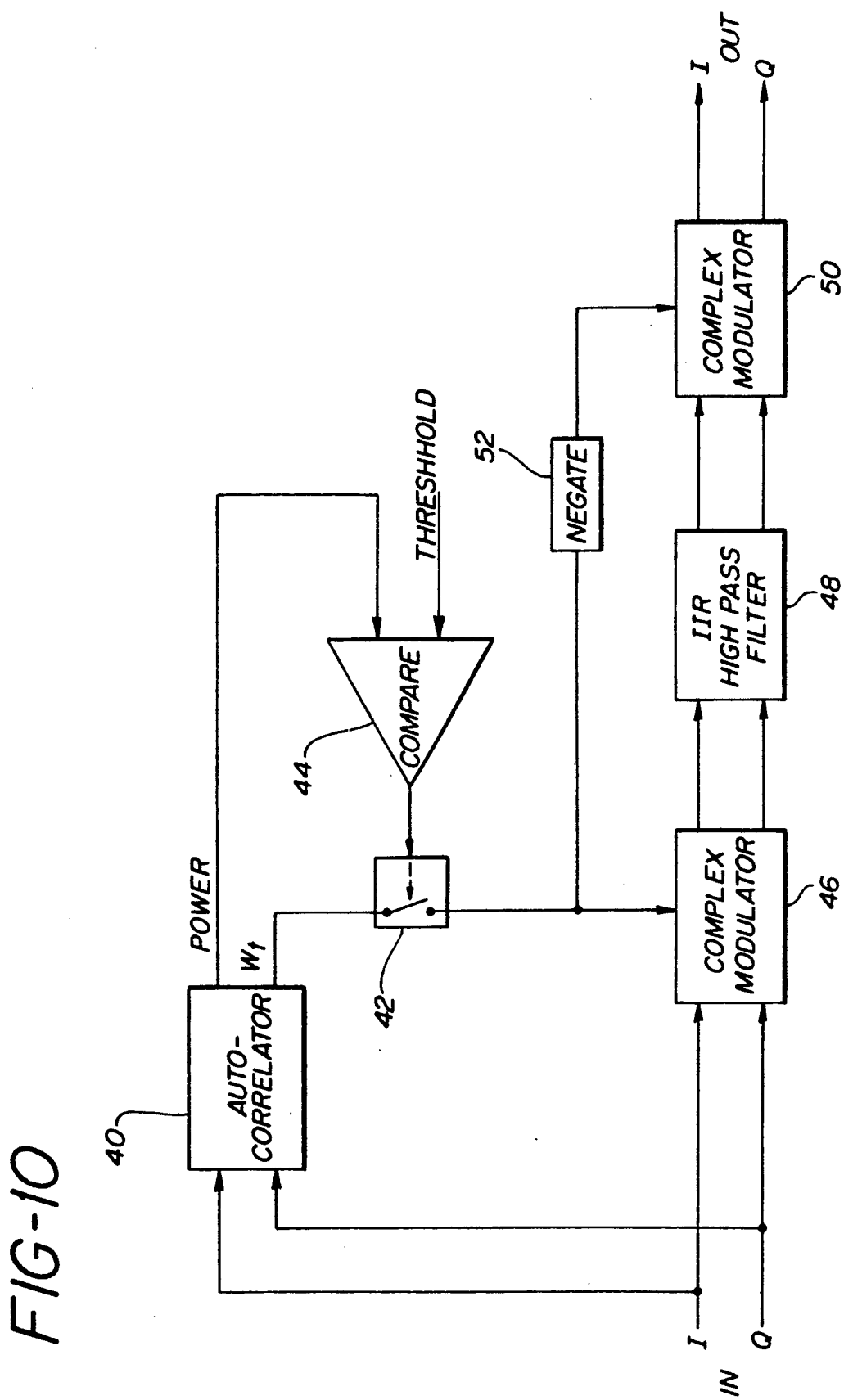
FIG. 10 is a block diagram of a preferred embodiment of a tissue motion signal component eliminator of the present invention.

A digital embodiment which provides all of the above features is shown in block diagram form in FIG. 10. In this embodiment, an autocorrelator 40 is used to determine $\omega_t$, and to determine spectral power. The spectral power value is compared with a threshhold value by the comparator 44, and the outcome of the comparison is used to open or close switch 42, controlling the frequency deviation $\omega_t$ by which the signals are modulated and remodulated. If the result of the comparison indicates that a tissue component is present, resulting either from moving or stationary tissue, switch 42 is closed and the frequency deviation of the tissue component $\omega_t$ is applied to complex modulator 46 to shift the spectrum, and to complex modulator 50 to shift the spectrum back after the tissue component has been eliminated. The complex modulator 50 receives a modulation value of the opposite sense as modulator 46 by reason of the inverting component 52. This technique is effective for removing both moving and stationary tissue components, as tissue motion components will be shifted in accordance with their deviation $\omega_t$, as will stationary tissue components for which $\omega_t$ will be found to be zero.

If the result of the comparison determines that no tissue component is present, the spectrum of FIG. 8, for instance, switch 42 is opened and the modulators 46 and 50 are effectively receiving modulating values of zero. The incoming data is shifted by a deviation of zero; that is, no shift is effected. The high pass filter 48 will filter the data as above, removing signal content about zero, but this will not adversely affect the outcome of the process as the effect is only to remove zero velocity (no flow) information. Modulator 50 will then remodulate the data by zero and the unaffected non-zero velocity flow information 32 is produced at the output for further processing. In a typical color flow implementation, data at the zero (no flow) location is represented in black, a representation which is unaffected by the elimination of data from this spectral location in FIG. 8.

What is claimed is:

1. In an ultrasonic diagnostic system, including means for receiving Doppler information signals from a subject which may include signal components from substantially stationary tissue and/or tissue motion components, which tissue does not flow through the subject, means for developing Doppler velocity information signals of materials capable of flowing through the subject in response to said received Doppler information signals, and means for formatting said Doppler velocity information signals for display, a method of removing effects of tissue motion from the information to be displayed comprising the steps of:
   (a) demodulating said received Doppler information signals to produce demodulated Doppler information signals;
   (b) discriminating said demodulated Doppler information signals for tissue motion signal components prior to the formatting of said Doppler velocity information signals for display;
   (c) eliminating said discriminated tissue motion signal components from said discriminated signals; and
   (d) providing velocity information signals to said formatting means from which effects of tissue motion have been removed.

2. The method of claim 1, wherein step (b) further comprises the step of determining the Doppler frequency of tissue motion signal components.

3. The method of claim 1, wherein step (b) comprises the step of discriminating signals containing Doppler information which signals are derived from a plurality of spatially related locations for tissue motion signal components prior to the formatting of said Doppler fluid velocity information for display.

4. The method of claim 1, wherein step (a) comprises the step of phase demodulating said received Doppler information signals to produce phase demodulated Doppler information signals.

5. The method of claim 4, further comprising the step of (e) formatting said velocity information signals from which effects of tissue motion have been removed by entering information corresponding to said velocity information in an image field.

6. The method of claim 1, wherein step (a) comprises the step of frequency demodulating said received Doppler information signals to produce frequency demodulated Doppler information signals.

7. In an ultrasonic diagnostic system, including means for receiving Doppler information signals from a subject which may include signal components from substantially stationary tissue and/or tissue motion components, which tissue does not flow through the subject, means for developing Doppler velocity information signals of materials capable of flowing through the subject in response to said received Doppler information signals, and means for formatting said Doppler velocity information signals for display, a method of removing effects of tissue motion from the information to be displayed comprising the steps of:
   (a) demodulating said received Doppler information signals using a known velocity reference signal;
   (b) discriminating signals containing Doppler information for tissue motion signal components prior to the formatting of said Doppler velocity information signals for display;
   (c) eliminating said discriminated tissue motion signal components from said discriminated signals; and (d) providing velocity information signals to said formatting means from which effects of tissue motion have been removed.

8. The method of claim 7, wherein step (c) further comprises the step of filtering signals containing Doppler information by means of a filter having a rejection band at the Doppler frequency of discriminated tissue motion signal components.

9. In an ultrasonic diagnostic system, including means for receiving Doppler information signals which may include signal components from substantially stationary tissue and/or tissue motion components, means for developing Doppler velocity information signals in response to said received Doppler information signals, and means for formatting said Doppler velocity information signals for display, a method of removing effects of tissue motion from the information to be displayed comprising the steps of:
  (a) demodulating said received Doppler information signals to produce demodulated Doppler information signals;
  (b) discriminating said demodulated Doppler information signals for tissue motion signal components prior to the formatting of said Doppler velocity information signals for display;
  (c) eliminating said discriminated tissue motion signal components from said discriminated signals; and
  (d) providing velocity information signals to said formatting means from which effects of tissue motion have been removed,
  wherein step (c) comprises the step of shifting said discriminated tissue motion signal components to a predetermined Doppler frequency band, and filtering said signals containing Doppler information by means of a filter having a rejection band corresponding to said predetermined Doppler frequency band.

10. In an ultrasonic diagnostic system, including means for receiving Doppler information signals which may include signal components from substantially stationary tissue and/or tissue motion components, means for developing Doppler velocity information signals in response to said received Doppler information signals, and means for formatting said Doppler effects of tissue motion from the information to be displayed comprising the steps of:
  (a) demodulating said received Doppler information signals using a known velocity reference signal;
  (b) discriminating signals containing Doppler information for tissue motion signal components prior to the formatting of said Doppler velocity information signals for display;
  (c) eliminating said discriminating tissue motion signal components from said discriminating signals; and
  (d) providing velocity information signals to said formatting means from which effects of tissue motion have been removed,
  wherein step (c) is preceded by the step of (a) determining the intensity of Doppler information signals and inhibiting the operation of step (c) if said Doppler information signal intensity does not exceed a predetermined criterion.

11. The method of claim 10, wherein step (a) comprises measuring the power of signals in the Doppler spectrum and inhibiting the operation of step (c) if the measured power does not exceed a predetermined threshold level.

12. An ultrasonic diagnostic system for processing Doppler information signals from a subject comprising:
  means for receiving fluid motion Doppler information signals from material capable of flowing through said subject which may be contaminated with components from substantially stationary tissue and/or tissue motion components, which tissue does not flow through the subject;
  means for demodulating said received Doppler information signals to produce demodulated Doppler information signals;
  means for discriminating the presence of said tissue motion components in said demodulated Doppler information signals;
  means for removing said discriminated tissue motion components;
  means for processing said fluid motion Doppler information signals from which tissue motion components have been removed to provide an image format containing fluid velocity information; and
  means for displaying said fluid velocity information.

13. The ultrasonic diagnostic system of claim 12, wherein said demodulating means comprises phase demodulating means, and said means for discriminating further comprises means for identifying the Doppler frequency location of tissue motion components.

14. The ultrasonic diagnostic system of claim 12, wherein said means for discriminating comprises means for discriminating the presence of tissue motion components in Doppler information signals, which signals are derived from a plurality of spatially related locations.

15. An ultrasonic diagnostic system for processing Doppler information signals from a subject comprising:
  means for receiving fluid motion Doppler information signals from material capable of flowing through said subject which may be contaminated with components from substantially stationary tissue and/or tissue motion components, which tissue does not flow through the subject;
  means for demodulating said received Doppler information signals to produce demodulated Doppler information signals;
  means for discriminating the presence of said tissue motion components in said demodulated Doppler information signals;
  means for removing said discriminated tissue motion components;
  means for processing said fluid motion Doppler information signals from which tissue motion components have been removed to provide an image format containing fluid velocity information; and
  means for displaying said fluid velocity information,
  wherein said means for removing comprises means for filtering Doppler information signals having a rejection band corresponding to tissue motion components.

16. An ultrasonic diagnostic system for processing Doppler information signals from a subject comprising:
  means for receiving fluid motion Doppler information signals from material capable of flowing through said subject which may be contaminated with components from substantially stationary tissue and/or tissue motion components, which tissue does not flow through the subject;
  means for demodulating said received Doppler information signals using a known velocity reference signal;

means for discriminating the presence of said tissue motion components in said Doppler information signals;

means for removing said discriminated tissue motion components;

means for processing said fluid motion Doppler information signals from which tissue motion components have been removed to provide an image format containing fluid velocity information referenced to said known velocity; and means for displaying said fluid velocity information.

17. The ultrasonic diagnostic system of claim 16, wherein said means for removing comprises first means for shifting discriminating tissue motion components to a predetermined Doppler frequency location, and means for filtering Doppler information signals having a rejection band corresponding to said predetermined Doppler frequency location.

18. The ultrasonic diagnostic system of claim 17, wherein said shifting means also shifts the Doppler frequency location of fluid motion Doppler information signals; and further comprising means for shifting said filtered Doppler information signals to shift fluid motion Doppler information signals to a Doppler frequency location exhibited by said fluid motion Doppler information signals prior to the operation of said first means for shifting.

19. An ultrasonic diagnostic system for processing Doppler information signals comprising:

means for receiving fluid motion Doppler information signals which may be contaminated with tissue signal components resulting from the presence of stationary or moving tissue;

means for discriminating the presence of said tissue signal components in said Doppler information signals, wherein components resulting from the presence of stationary tissue are located at a predetermined Doppler frequency location;

means for shifting discriminated tissue signal components not located at said predetermined Doppler frequency location to said predetermined Doppler frequency location;

means for shifting fluid motion Doppler information signals to the Doppler frequency locations exhibited by said fluid motion Doppler information signals prior to the operation of said first shifting means; and means for processing said fluid motion Doppler information signals from which tissue components have been removed.

20. The ultrasonic diagnostic system of claim 19, further comprising means, responsive to said discriminating means, for inhibiting said first shifting means in the absence of tissue signal components.

* * * * *